(12) United States Patent
Bager et al.

(10) Patent No.: US 7,935,095 B2
(45) Date of Patent: *May 3, 2011

(54) OSTOMY MOUNTING WAFER AND A METHOD OF PREPARING IT

(75) Inventors: Kim Bager, Lyngby (DK); Ingrid Laesoe Fink, Lynge (DK)

(73) Assignee: Coloplast A/S, Humblebaek (DK)

( * ) Notice: Subject to any disclaimer, the term of this patent is extended or adjusted under 35 U.S.C. 154(b) by 695 days.

This patent is subject to a terminal disclaimer.

(21) Appl. No.: 10/577,054

(22) PCT Filed: Oct. 21, 2004

(86) PCT No.: PCT/DK2004/000728
§ 371 (c)(1),
(2), (4) Date: Apr. 24, 2006

(87) PCT Pub. No.: WO2005/039861
PCT Pub. Date: May 6, 2005

(65) Prior Publication Data
US 2007/0135782 A1    Jun. 14, 2007

(30) Foreign Application Priority Data
Oct. 24, 2003   (DK) .................................. 2003 01571

(51) Int. Cl.
*A61F 5/44* (2006.01)
(52) U.S. Cl. ........ 604/337; 604/338; 604/332; 604/335; 604/336; 604/339; 604/341; 604/342; 604/343; 604/344

(58) Field of Classification Search .................. 604/337, 604/338, 332, 335–336, 339, 341, 342, 343, 604/344
See application file for complete search history.

(56) References Cited

U.S. PATENT DOCUMENTS

| | | | |
|---|---|---|---|
| 4,636,609 A | * | 1/1987 | Nakamata ................ 219/121.64 |
| 5,893,959 A | | 4/1999 | Muellich |
| 6,966,901 B2 | | 11/2005 | Leisner et al. |

(Continued)

FOREIGN PATENT DOCUMENTS

DE    10211782    9/2003

(Continued)

OTHER PUBLICATIONS

XP-000952346 "Use of Infrared Dyes for Transmission Laser Welding Of Plastics", Jones et al, ANTEC 2000, pp. 1166-1170.

*Primary Examiner* — Tatyana Zalukaeva
*Assistant Examiner* — Ginger T Chapman
(74) *Attorney, Agent, or Firm* — Coloplast Corp., Coloplast A/S; Daniel G. Chapik; Nicholas R. Baumann

(57) ABSTRACT

An ostomy body side mounting wafer and a method of preparing the ostomy body side mounting wafer, where the wafer is assembled from two parts using laser welding. The laser light is provided through one of the parts having a low or lower absorption of the laser light. The other part has a higher absorption of the laser light, whereby the interface between the two parts is heated at the welding zone(s) of the laser light. In this manner, an assembly is obtained independently of the thicknesses of the materials and even close to openings or other edges.

13 Claims, 3 Drawing Sheets

U.S. PATENT DOCUMENTS

2003/0093042 A1 * 5/2003 Leisner et al. ................ 604/337

FOREIGN PATENT DOCUMENTS

| EP | 1 108 404 | | 6/2001 |
| EP | 1 108 404 A1 | * | 6/2001 |
| EP | 1 275 357 | | 1/2003 |
| WO | WO 96/38106 | * | 12/1996 |
| WO | WO 00/20157 | | 4/2000 |
| WO | WO 00/30576 | | 6/2000 |
| WO | WO 00/66346 | | 11/2000 |
| WO | WO 02/00144 | | 1/2002 |
| WO | WO 02/00144 A1 | * | 3/2002 |
| WO | WO 2005/039861 A2 | * | 6/2005 |

* cited by examiner

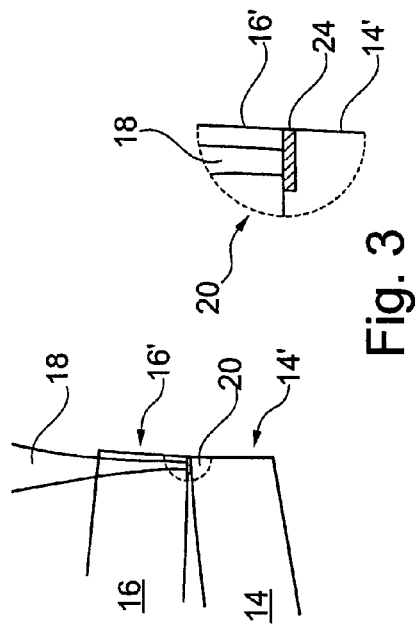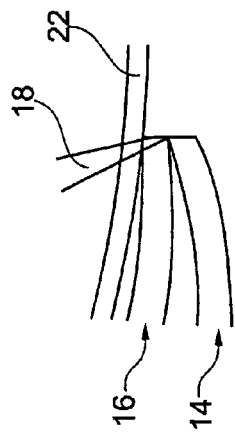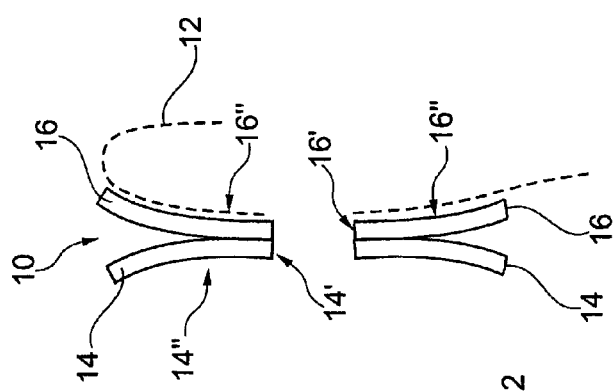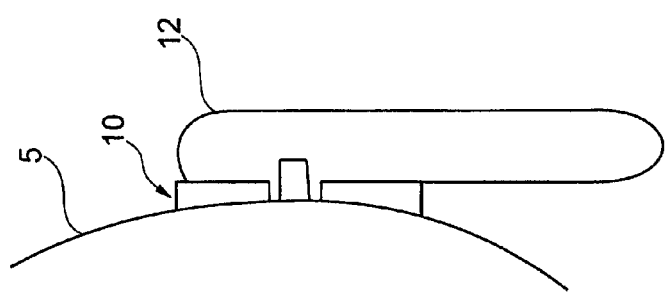

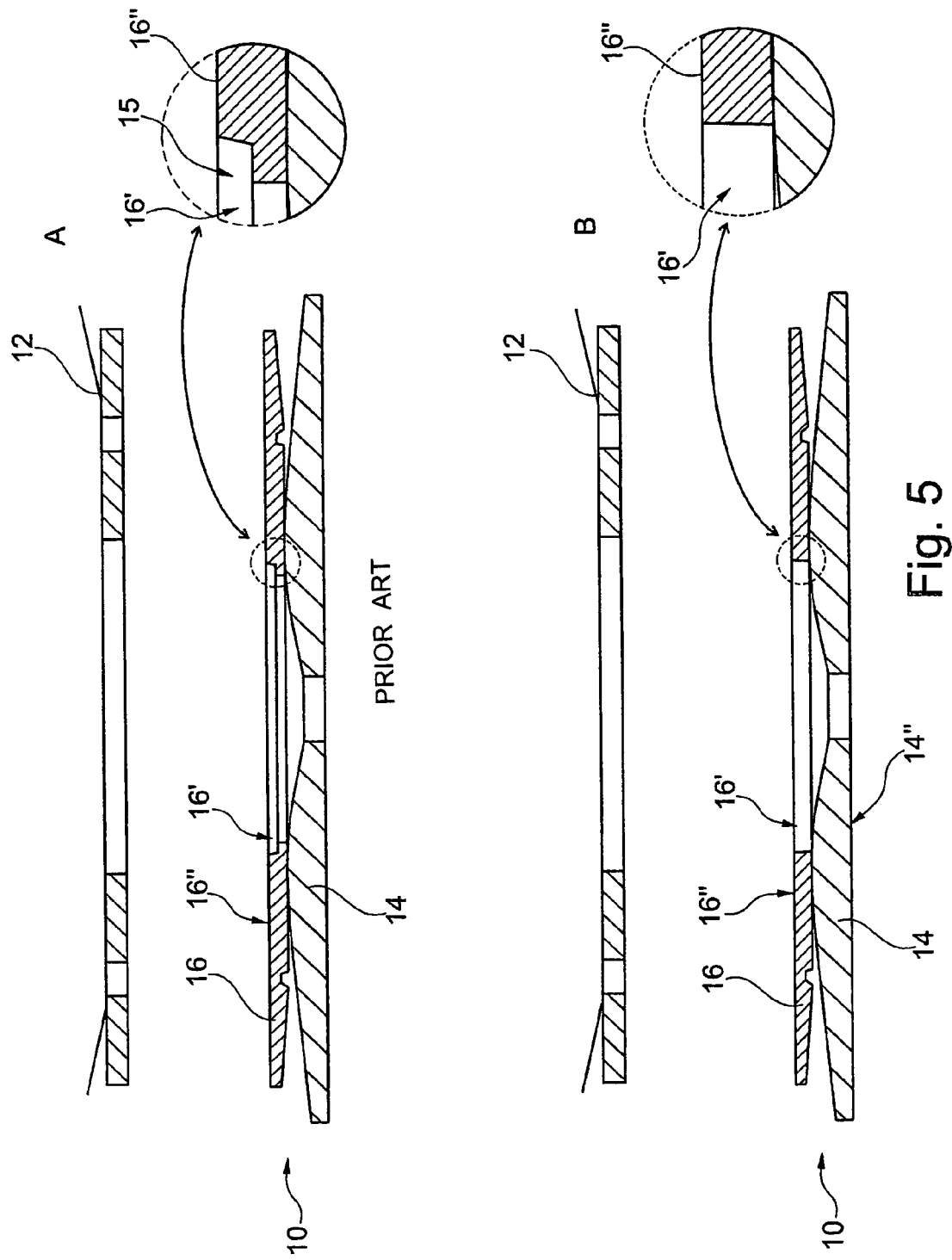

OSTOMY MOUNTING WAFER AND A METHOD OF PREPARING IT

This is a nationalization of PCT/DK2004/000728 filed 21 Oct. 2004 and published in English.

BACKGROUND OF THE INVENTION

1. Field of the Invention

The present invention relates to an ostomy wafer which is the part of an ostomy bag set mounted to the person and to which detachable ostomy bags may be mounted.

2. Description of the Related Art

Normally, in order to obtain suitable flexibility, ostomy mounting wafers are prepared by fixing two parts to each other, where one part is adapted to be fixed to the person and the other part is adapted to form a landing zone for the ostomy bag. These parts are attached at the ostomy opening. However, this attachment must both be strong and sealed in order to prevent leaking.

Hitherto, this assembly/sealing has been performed by either using adhesives or heat welding.

Using adhesives provides a wider range of possibilities as to the actual shape of the attachment area and the thickness of the materials at the zones of attachment. However, for a number of reasons, the use of adhesives has been rejected as the proper way of attaching these parts. One such reason is the fact that the adhesive may present an environmental problem. Also, the use of adhesives adds a number of demands as to the adhesive and other materials useable. In addition, the long term stability of the adhesive connection is questionable.

Heat sealing/welding, on the other hand, avoids the use of adhesives but it results in the parts being deformed at the sealing due to the heat and pressure applied. In addition, the materials must fulfill certain requirements as to melting points and in particular the material thicknesses in the welding zone. Thus, both the dimensions required by the welding and the undesired dimension changes caused by the welding will provide weak zones and generally prevent the element from being useful for connection purposes in the area around the welding zone.

SUMMARY OF THE INVENTION

The present invention relates to a manner of attaching these parts in a manner where thicknesses may vary within much wider boundaries, where the outer surfaces at the attachment zones may be used for e.g. fastening the bag, and where a much wider selection of materials may be applied.

In a first aspect, the invention relates to a method of preparing a body side mounting wafer for attachment to a person and an ostomy bag, the method comprising:

providing a first part having a first surface having one or more means adapted to be attached to or fixed to a body part of the person, and a second, opposite, surface, the first part having a first absorption coefficient at a predetermined wavelength of electromagnetic radiation, providing a second part having a first surface having one or more means adapted to be attached to or fixed to the ostomy bag and a second, opposite, surface, the second part having a second absorption coefficient at the predetermined wavelength of electromagnetic radiation, the first and second absorption coefficients being different, positioning the first and second parts so as to abut at one or more zones of the second surface of the second part and of the first part, at least part of one zone being aligned with the attaching/fixing means of the first and/or second parts, and providing electromagnetic radiation, comprising radiation of the predetermined wavelength, through that of the first and second parts having the lowest absorption coefficient to the one or more zones so as to heat the other of the first and second parts at the one or more zones in order to, upon cooling, fix the first and second parts to each other.

In this respect, the attachment to the user and to the bag may be any desired type of attachment, such as using adhesives, mechanical fastening means, snap fit fastening means such as hook-and-loop fasteners, hook-like fasteners, or the like. Normally, the body side wafer will be used with a number of bags before replacement, so that the attaching/fixing means of the second part are adapted to attach/fix the bag in a detachable manner, but this is not a requirement.

Naturally, a single weld, such as an elongated, continuous weld, may comprise several zones. Alternatively or additionally, it may be desired to provide a number of discrete welds.

In the present context, one or more of the zones are preferably positioned directly below (projected in a plane of the first surface of the second part) the attaching/fixing means of the first surface of the second part. This eliminates one of the problems of the prior art heat welding in that it is desired to be able to use this area also for attaching the bag. Thus, preferably, the step of positioning the parts comprises abutting the first and second parts at the one or more zones of the second surfaces, where a projection of the zones and the attaching/fixing means of the first surfaces of both the first and second parts, onto a general plane of the first surface of the second part, overlap.

Also, preferably, the first and second absorption coefficients are not merely different, but the lower absorption coefficient preferably is so low that no or insignificant melting occurs at the areas of this part through which the radiation travels toward the zones to be heated. Also, preferably, the absorption coefficient of the other material is high enough to primarily absorb the radiation in the vicinity of the zone(s) of the second surface(s) in order to obtain a localized heating and not a heating through a larger extension of that part (the extension being in the direction of the radiation).

Preferably, the first part has a first opening, the second part has a second opening, and the positioning step comprises positioning the first and second parts so that the first and second openings coextend. In this context, "coextend" will mean that the edges of the openings overlap or that centre axes thereof overlap and coextend.

In this situation, a preferred embodiment is one wherein the step of providing the second part comprises providing a second part where the attaching/fixing means comprise a surface adapted to engage an adhesive part of the ostomy bag, the surface extending to an edge of the second opening, and wherein at least one of the one or more zones is positioned in a vicinity of the edge of the second opening. Thus, the full surface may be used for engaging with the bag while still being able to provide the engagement/sealing close to or at the opening. In this context, "vicinity" preferably means that the sealing leaves no or as little as possible room, seen from the openings, between the first and second parts for housing impurities. Thus, preferably the melting/heating takes place as close to the edge as possible.

Naturally, other zones, in addition to that/those at the edge of the opening, may be selected for attachment in order to obtain a desired flexibility, attachment, and sealing of the wafer.

It may be desired to select materials for use in the first and second parts which are not optimized for this welding/melting process. In that situation, the step of providing that of the first and second parts having the highest absorption coefficient may comprise providing the respective part with:
- a material having the first or second absorption coefficient at least at the one or more zones, and,
- at other parts of the respective part, another material having a third absorption coefficient at the predetermined wavelength.

The third absorption coefficient may be lower than the highest of the first and second absorption coefficients. Thus, the material having the higher absorption coefficient may be situated mainly at the zones while the material (that with the third absorption coefficient) at other parts of the respective part may have a lower absorption coefficient but fulfil other requirements to the part (flexibility, bonding properties etc). In this manner, the high absorption coefficient and thereby heating is still achieved.

This high absorption coefficient material may be added in a layer so thin that it actually is melted and vanishes into (e.g. reacts with) the surrounding material during melting/welding.

Preferably, the radiation is IR or NIR radiation, such as where the predetermined wavelength is determined within the interval of 0.7-6 μm, such as 0.8-1.1 μm. Also, preferably the radiation is laser radiation. Naturally, however, radiation having other wavelengths may be provided in addition to the radiation at the predetermined wavelength, even though it may bring about undesired heating of the materials with the low absorption coefficient An interesting embodiment is one comprising, during the step of providing the radiation, maintaining, using a fastening means, the first and second parts in the abutting position, the step of providing the radiation comprising providing the radiation through the fastening means. This fastening means may have a fourth absorption coefficient at the predetermined wavelength, which fourth absorption coefficient ensures that the intensity loss of the radiation when travelling through the fastening means is sufficiently low to leave sufficient radiation for the welding/melting and to not damage the fastening means.

In that embodiment, the radiation may be provided through the fastening means while maintaining the first and second parts in the desired position. In this manner, full freedom is obtained to select how to hold the first and second parts during the welding/radiation. If positions for the fastening means are selected where the radiation is provided to the zone(s), the fastening means may be selected with a suitable (low) absorption coefficient to allow transmission of the radiation there through without excessive loss of radiation intensity and excessive heating of the fastening means.

A second aspect of the invention relates to a body side mounting wafer for attachment to a person and an ostomy bag, the wafer comprising:
- a first part having a first surface adapted to be attached to or fixed to a body part of the person and a second, opposite surface,
- a second part having a first surface adapted to be attached to the ostomy bag and a second, opposite surface,
- one or more welds formed at one or more welding zones between the second surfaces of the first part and the second part, at least one weld zone extending over a first distance in a radial direction, wherein the first surface of the second part is at least substantially smooth at the at least one weld zone and over a second distance extending over the at least one weld zone, the second distance extending in the radial direction and being at least 1.5 times the first distance.

In this respect, a radial direction is e.g. a direction from an opening (for a stoma) of the wafer and away there from.

The first distance may be quite small, such as in the situation where the weld is a laser weld provided in a single line around the opening of the wafer (for the stoma). In that situation, the first distance will be the width of the weld.

Naturally, multiple welds may be provided along the radial direction as e.g. concentric circles, and the weld may have any extent along that direction.

The smooth surface is especially desired in order to ensure that this surface fits a corresponding surface of the ostomy bag for attachment or engagement to the wafer.

In a preferred embodiment, "smooth" will mean that the first part has a general thickness profile, which profile describes the desired thickness along a specific direction in the part(s), such as the radial direction. In this situation, the actual thickness, over the second distance, should deviate less than 10%, such as less than 5%, preferably less than 1.5% from the thickness of the general thickness profile over the distance. Thus, a relatively small deviation is accepted from the smooth thickness profile. The reason for this is that sharp edges or sharp bends in the surface or thickness profile tend to form weakness zones at which the material may break upon stressing.

In the situation of an adhesive coupling, the smooth surface should preferably be so smooth that the adhesive, and/or a means of the bag holding the adhesive, preferably is able to take up any variations in the surface from the intended shape of the surface. In that situation, the adhesive coupling will function and seal the inside of the bag from the outside thereof.

Consequently, the desired smoothness may vary with different types of adhesive couplings. Some adhesive couplings comprise a relatively deep layer of adhesive on a very resilient base, such as a foam. This type of coupling is able to take up larger dimensional variations than a smaller layer of adhesive on a stiff base.

In the situation where a linear or flat first surface is desired in the second part, the surface may be smooth, if no 2 mm part of the first surface of the second part, in a cross section along the radial direction and over the second distance, has any part deviating more than 0.2 mm from a flat shape fitted to the 2 mm part.

This is a simple manner of determining the smoothness of a flat surface: no part of the surface, along the radial direction and over the relevant second distance extending over the weld, may, over a 2 mm stretch, have a part extending more than 0.2 mm above or below a linear fit to the 2 mm part. This extending is determined at a right angle to the linear fit. Any other length than 2 mm could be chosen, as the overall aim is to avoid sharp dimension changes which may give rise to leakage due to the bag side attachment means and the smooth surface not engaging sufficiently.

Naturally, a less smooth surface may simply increase the demands on the bag side attachment means. Thus, preferably, no 2 mm part has a part extending more than 0.4 mm, such as 0.8 mm.

Naturally, the second distance may be larger than the above 1.5 times, in that this distance describes a minimum surface which may be used for attaching or engaging a bag. Thus, the second distance may extend at least 5 times the first distance, such as at least 10 times the first distance, preferably at least 20 times the first distance, such as at least 100 times the first distance.

In a third aspect, the invention relates to a body side mounting wafer for attachment to a person and an ostomy bag, the wafer comprising:
- a first part having a first surface having one or more means adapted to be attached to or fixed to a body part of the person and a second, opposite surface,
- a second part having a first surface having one or more means adapted to be attached to the ostomy bag and a second, opposite surface,
- one or more welds formed at one or more welding zones between the second surfaces of the first part and the second part, wherein the one or more means of the first surface of the second part are aligned with at least part of the zones.

As mentioned above, the alignment preferably is a positioning where the zones are positioned so that, when projected onto a plane of the first surface, they overlap or are positioned opposite to the attaching/fixing means.

As mentioned above, in a preferred embodiment, the first surface of the first and/or second part may be a surface to be used as a landing zone for an adhesive coupling especially when:
- the first part has a first opening,
- the second part has a second opening,
- the zones are positioned in a vicinity of the edge of the second opening.

Alternatively, the attaching/fixing means of especially the second part may be adapted to snap-fit to corresponding means on the ostomy bag. This is the traditional alternative to the adhesive coupling which, in certain circumstances, has disadvantages when securing and re-securing adhesive bags thereto.

A fourth aspect of the invention relates to an apparatus for performing the above method, the apparatus comprising:
- fastening means for receiving and holding the first and second parts in the abutting relationship and
- means for providing the radiation to the one or more zones.

As mentioned, preferably, the radiation providing means are adapted to provide the radiation through the fastening means.

A last aspect of the invention relates to an apparatus for assembling the above body side wafer, the apparatus comprising:
- fastening means for maintaining the first and second parts in a predetermined, abutting relationship and
- means for providing the electromagnetic radiation to the zone(s) to form the weld(s).

It should be noted that the present manner of attaching the two parts to each other may be made virtually independent on the shapes of the openings/fastening positions, the cross sectional thickness and shape of the parts etc. Thus, a much wider selection of shapes and positions of engagement may be obtained.

BRIEF DESCRIPTION OF THE DRAWINGS

In the following, a preferred embodiment of the invention will be described with reference to the drawing, wherein FIG. 1 illustrates an ostomy wafer attached to a person and an ostomy bag, FIG. 2 illustrates the wafer in more detail, FIG. 3 illustrates laser welding of the wafer, FIG. 4 illustrates laser welding of the wafer through a holding means, FIG. 5 illustrates a specific embodiment and a corresponding prior art wafer.

DETAILED DESCRIPTION OF THE PREFERRED EMBODIMENTS

Figure 6:
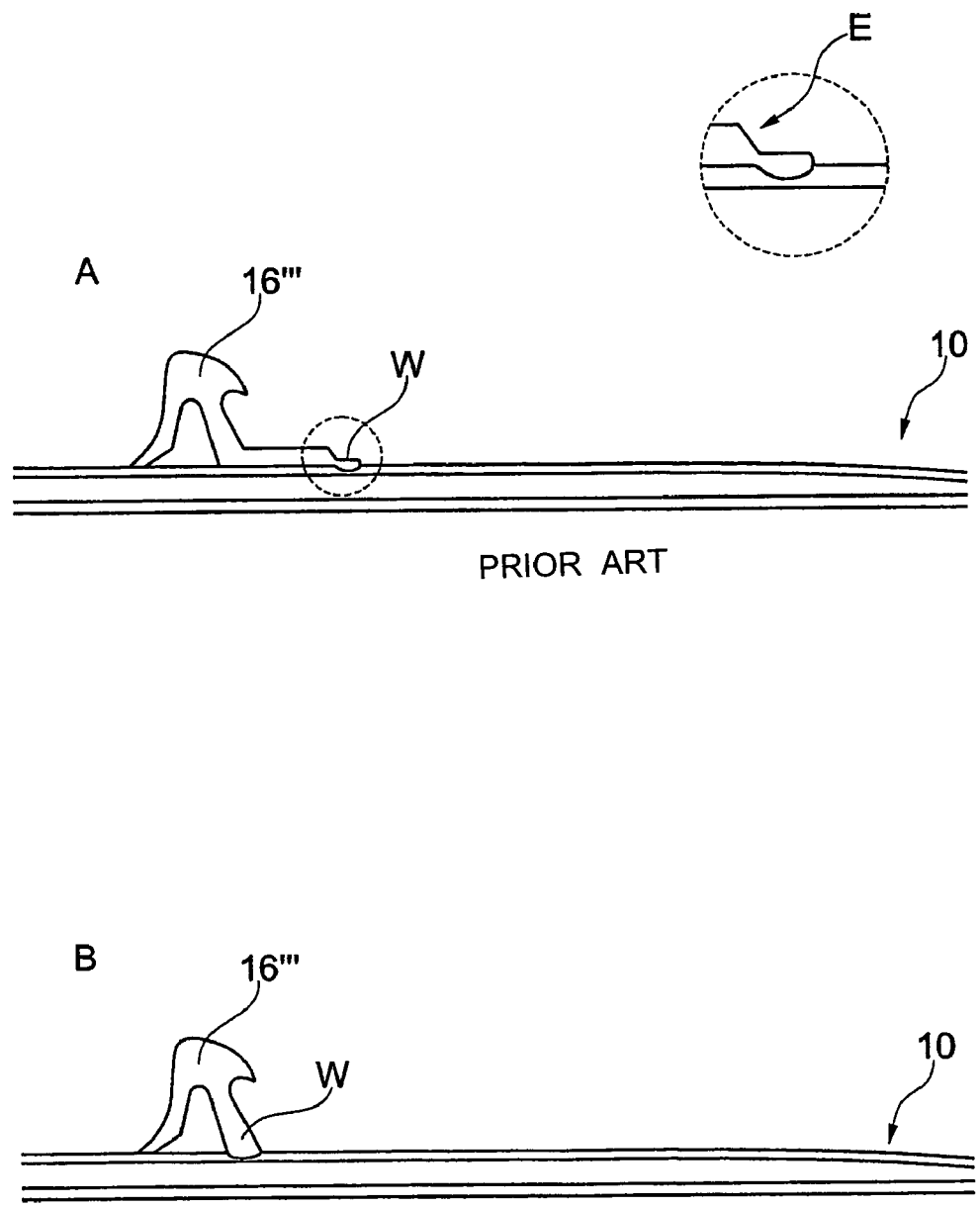
FIG. 6 illustrates another embodiment of an attaching/fixing means and a corresponding prior art means.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

FIG. 1 illustrates an ostomy bag 12 attached to a body side mounting wafer 10 attached to a person 5 and around a stoma. The wafer serves the purpose of, consecutively, attaching a number of bags to the person without having to detach the wafer from the skin of the person.

The wafer (see FIG. 2) actually is formed of two parts 14 and 16 which each has an opening for the stoma; the openings have edges 14' and 16'. In the present embodiment, the edges 14' and 16' are coextending.

Naturally, one of the parts 14 and 16 may have an opening with a larger diameter than the other. In that situation, the welding may be performed at the edge of the higher-diameter part in order to ensure that no openings or cavities exist for housing impurities.

The surface 14" of the wafer is for attachment to the person and the surface 16" is for attachment to the bag. Normally, the attachment to the user is obtained using an adhesive. Attachment to the bag may be obtained with a variety of means, such as adhesives or hook-like means engaging with similar means or edges on the bag, e.g.

It is seen that any part of the surface 16" may be used for engaging with the bag 12.

The actual laser welding is illustrated in FIG. 3, where the laser beam is directed through the part 16 to a zone at an interface between the parts 14 and 16 and close to the edges 14' and 16'.

In this embodiment, the part 16 has the lowest absorption coefficient at the wavelength of the laser radiation 18, whereby the radiation is transmitted through the part 16 with no or only very little heating of the part 16. When the radiation enters the part 14, having a higher absorption coefficient, the material of the part 14 will heat and melt at the interface (and preferably also the neighbouring material of the part 14), whereby, upon cooling, the two parts 14 and 16 will be welded together.

When the welding zone is positioned that close to the edges 14' and 16', the materials will be welded at the edges, whereby no openings or cracks exist for housing impurities.

As illustrated in the enlargement of FIG. 3, a material 24 may be introduced between the parts 14 and 16 or at the surface of the part 14. This may be useful when the absorption coefficient of the material 14 is not high enough for providing a suitable absorption and thereby heating and melting. In that situation, a material 24, having a higher absorption coefficient may be introduced for providing the temperature rise and thereby the actual welding. In this manner, the remaining material of the part 14 may be selected more freely in order to accommodate other requirements, such as bonding requirements and flexibility requirements.

Naturally, this setup may be reversed and the radiation transmitted to the interface through the part 14.

FIG. 4 illustrates a holding means 22 holding the parts 14 and 16 before and during welding. When it is desired to hold the parts at a position where it is also desired to provide the radiation 18, the holding means 22 may be selected to have a sufficiently low absorption coefficient to transmit the radiation to the interface without being damaged (heated or the like) and without damping the radiation too much.

The selected shape and position of the holding means 22 will depend on a number of factors, such as the shapes of the parts 14 and 16, the overall shape of the wafer 10, the positions of attachment/welding. However, providing this manner of attachment and the absorption coefficient of the holding means, this shape and position may be selected freely.

FIG. 5 illustrates, as FIG. 5A at the top, a specific prior art product having a wafer 10 and a bag 12 adapted to form an adhesive connection.

This product has been heat welded at the centre edge 16', which may be seen in the enlarged portion which illustrates that a depression 15 is preformed to allow the heat welding. When welded, this depression will be emphasized and in most cases have an irregular surface. In this manner, the surface 16" may not be used as a landing zone for the bag all the way over the welding and all the way to the edge 16' of the opening in the part 16.

In FIG. 5B, the same product is illustrated with a laser weld, where it is seen that no preformed depression is needed and no change of shape takes place, whereby the surface 16" is useful all the way to the edge 16' of the opening of the part 16.

FIG. 6 illustrates a cross section of another means for attaching a bag to the wafer 10. A ring 16''' having this cross section is provided around the opening of the wafer 10. In FIG. 6A, illustrating a prior art wafer, the ring is attached at a welding W positioned away from the actual ring 16''' in order to heat weld the ring and not damage the ring. However, the welding will depress the material of the ring and thereby introduce a sharp edge, E, which is a weak spot of the ring.

Thus, not only will the heat welding W provide a weak spot of the ring, it also requires the ring to be larger in order to provide space for the weld.

In FIG. 6B, the same ring is used in a product according to the invention in which the ring is laser welded to the plate. Firstly, the laser welding W may be positioned directly under the ring 16''', and secondly, it is seen that the ring extends over a much smaller area of the plate.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A body side mounting wafer for attachment to a person and an ostomy bag, the wafer comprising:
    a first part having a first surface adapted to be attached to or fixed to a body part of the person and a second, opposite surface;
    a second part having a first surface adapted to be attached to the ostomy bag and a second, opposite surface;
    one or more welds formed at one or more welding zones between the second surfaces of the first part and the second part such that the second surfaces melt and the first surfaces do not melt, at least one weld zone extending over a first distance in a radial direction; and
    the first surface of the second part being at least substantially smooth at the at least one weld zone and over a second distance extending over the at least one weld zone so that said first surface of said second part is suitable for adhesive attachment to the ostomy bag at said at least one weld zone and including at said one or more welds, the second distance extending in the radial direction and being at least 1.5 times the first distance.

2. The body side mounting wafer according to claim 1, wherein no 2 mm part of the first surface of the second part, in a cross section along the radial direction and over the second distance, has any part deviating more than 0.2 mm from a flat shape fitted to the 2 mm part.

3. The body side mounting wafer according to claim 1, wherein:
    the first part has a first opening;
    the second part has a second opening;
    the zones being positioned in a vicinity of the edge of the second opening.

4. The body side wafer according to claim 1, further comprising an apparatus for assembling said body side wafer that includes:
    a fastening element for maintaining the first and second parts in a predetermined, abutting relationship; and
    an element for providing electromagnetic radiation to the zone(s) to form the weld(s).

5. The body side mounting wafer according to claim 1, wherein:
    the first part has a first opening;
    the second part has a second opening; and
    the zones are positioned in a vicinity of the edge of the second opening.

6. The body side mounting wafer according to claim 1, wherein the weld is a laser weld provided in a single line provided around an opening of the wafer, said first distance being the width of the weld.

7. The body side mounting wafer according to claim 1, wherein multiple welds are provided along the radial direction.

8. The body side mounting wafer according to claim 1, wherein the first part has a general thickness profile which describes a desired thickness along a specific direction in the part(s), where the actual thickness, over the second distance, deviates less than 10% from the thickness of the general thickness profile over the distance.

9. The body side mounting wafer according to claim 1, wherein the first surface of the second part is adapted to form an adhesive coupling to the ostomy bag, and wherein the smooth surface is so smooth that the adhesive, and/or a component of the bag holding the adhesive, is able to take up any variations in the surface from the intended shape of the surface.

10. The body side mounting wafer according to claim 1, wherein the first surface of the second part has no 2 mm part thereof, in a cross section along the radial direction and over the second distance, in which any part deviates more than 0.2 mm from a flat shape fitted to the 2 mm part.

11. The body side mounting wafer according to claim 1, wherein the first part has a first absorption coefficient at a predetermined wavelength of electromagnetic radiation, the second part has a second absorption coefficient at the predetermined wavelength of electromagnetic radiation, the first and second absorption coefficients being different.

12. The body side mounting wafer according to claim 11, wherein the lower of the first and second absorption coefficients is so low that no or insignificant melting occurs at the areas of this part through which the radiation travels toward the zone(s) to be welded, and wherein a higher of the first and second absorption coefficients is high enough to primarily absorb the radiation in the vicinity of the zone(s) of the second surfaces in order to obtain a localized heating and not a heating through a larger extension of that part.

13. A body side mounting wafer for attachment to a person and an ostomy bag, the wafer comprising:
- a first part having a first surface adapted to be attached to or fixed to a body part of the person and a second, opposite surface;
- a second part having a first surface adapted to be attached to the ostomy bag and a second, opposite surface;
- a weld zone formed between the second surfaces of the first part and the second part such that the second surfaces melt and the first surfaces do not melt to allow the first surface of the second part to be substantially smooth at the weld zone so that said first surface of said second part is configured for improved adhesive attachment to the ostomy bag.

* * * * *